United States Patent
Rock

(10) Patent No.: US 11,426,479 B2
(45) Date of Patent: Aug. 30, 2022

(54) DEVICE AND METHOD FOR STERILIZATION OF INSTRUMENTS AND SURFACES

(71) Applicant: Gail Rock, Ottawa (CA)

(72) Inventor: Gail Rock, Ottawa (CA)

(*) Notice: Subject to any disclaimer, the term of this patent is extended or adjusted under 35 U.S.C. 154(b) by 343 days.

(21) Appl. No.: 15/974,115

(22) Filed: May 8, 2018

(65) Prior Publication Data

US 2018/0250429 A1 Sep. 6, 2018

Related U.S. Application Data

(62) Division of application No. 13/839,011, filed on Mar. 15, 2013, now abandoned.

(60) Provisional application No. 61/722,597, filed on Nov. 5, 2012.

(51) Int. Cl.
| | |
|---|---|
| *A61L 2/10* | (2006.01) |
| *A61L 2/18* | (2006.01) |
| *A61L 2/00* | (2006.01) |
| *A61L 2/08* | (2006.01) |
| *A61L 2/26* | (2006.01) |

(52) U.S. Cl.
CPC .............. *A61L 2/18* (2013.01); *A61L 2/0088* (2013.01); *A61L 2/08* (2013.01); *A61L 2/10* (2013.01); *A61L 2/26* (2013.01); *A61L 2202/11* (2013.01); *A61L 2202/24* (2013.01)

(58) Field of Classification Search
CPC .............. A61L 2/088; A61L 2/18; A61L 2/10
See application file for complete search history.

(56) References Cited

U.S. PATENT DOCUMENTS

| | | |
|---|---|---|
| 4,124,598 A | 11/1978 | Hearst et al. |
| 4,169,204 A | 9/1979 | Hearst et al. |
| 4,402,318 A | 9/1983 | Swartz |
| 4,612,007 A | 9/1986 | Edelson |
| 4,683,889 A | 8/1987 | Edelson |
| 4,693,981 A | 9/1987 | Wiesehahn et al. |

(Continued)

FOREIGN PATENT DOCUMENTS

| | | |
|---|---|---|
| EP | 0 066 886 A2 | 12/1982 |
| EP | 0 196 515 A1 | 10/1986 |
| WO | 03/063915 A1 | 8/2003 |

OTHER PUBLICATIONS

Extended European Search Report dated Jan. 22, 2014, issued by the European Patent Office in corresponding European Application No. 13191427.7. (4 pages).

(Continued)

*Primary Examiner* — Donald R Spamer
(74) *Attorney, Agent, or Firm* — Buchanan Ingersoll & Rooney P.C.

(57) ABSTRACT

A device for decontaminating a medical device, the device including a compartment adapted to contain a medical device and a solution, the solution comprising a photoactivatable substance; and a light system providing 360 degrees of exposure to the compartment. Also, a method for decontaminating a medical device, the method including placing a medical device in a compartment with a solution, the solution comprising a photoactivatable substance; incubating the medical device in the solution to allow the photoactivatable substance to attach to pathogens; and exposing the compartment to 360 degrees of light exposure to activate the photoactivatable substance.

15 Claims, 8 Drawing Sheets

(56) References Cited

U.S. PATENT DOCUMENTS

| | | |
|---|---|---|
| 4,727,027 A | 2/1988 | Wiesehahn et al. |
| 4,915,683 A | 4/1990 | Sieber |
| 5,041,078 A | 8/1991 | Matthews et al. |
| 5,106,619 A | 4/1992 | Wiesehahn et al. |
| 5,120,649 A | 6/1992 | Horowitz et al. |
| 5,232,844 A | 8/1993 | Horowitz et al. |
| 5,304,113 A | 4/1994 | Sieber et al. |
| 5,342,752 A | 8/1994 | Platz et al. |
| 5,360,734 A | 11/1994 | Chapman et al. |
| 5,418,130 A | 5/1995 | Platz et al. |
| 5,516,629 A | 5/1996 | Park et al. |
| 5,545,516 A | 8/1996 | Wagner |
| 5,587,490 A | 12/1996 | Goodrich, Jr. et al. |
| 5,607,924 A | 3/1997 | Magda et al. |
| 5,654,443 A | 8/1997 | Wollowitz et al. |
| 5,709,991 A | 1/1998 | Lin et al. |
| 5,714,328 A | 2/1998 | Magda et al. |
| 5,798,238 A | 8/1998 | Goodrich, Jr. et al. |
| 6,165,711 A | 12/2000 | Dorner et al. |
| 6,245,570 B1* | 6/2001 | Grimm ............... A61J 1/10 250/453.11 |
| 6,258,577 B1 | 7/2001 | Goodrich, Jr. et al. |
| 6,268,120 B1 | 7/2001 | Platz et al. |
| 6,277,337 B1 | 8/2001 | Goodrich, Jr. et al. |
| 7,901,673 B2 | 3/2011 | Lockerbie et al. |
| 2008/0265179 A1 | 10/2008 | Havens et al. |
| 2010/0072399 A1 | 3/2010 | Street et al. |
| 2010/0133203 A1* | 6/2010 | Walker ............... B65B 55/08 210/748.11 |
| 2013/0256560 A1* | 10/2013 | Yerby ............... A61L 2/10 250/455.11 |
| 2014/0127077 A1 | 5/2014 | Rock |
| 2018/0250429 A1 | 9/2018 | Rock |

OTHER PUBLICATIONS

"Surgery". Wikipedia. Historical version from Nov. 7, 2011.

Office Action (Examination Search Report) dated Sep. 16, 2019, by the Canadian Intellectual Property Office in Canadian Patent Application No. 2,832,380, (3 pages).

Office Action (Communication pursuant to Article 94(3) EPC) dated Jan. 13, 2021, by the European Patent Office in corresponding European Application No. 13 191 427.7-1104. (5 pages).

* cited by examiner

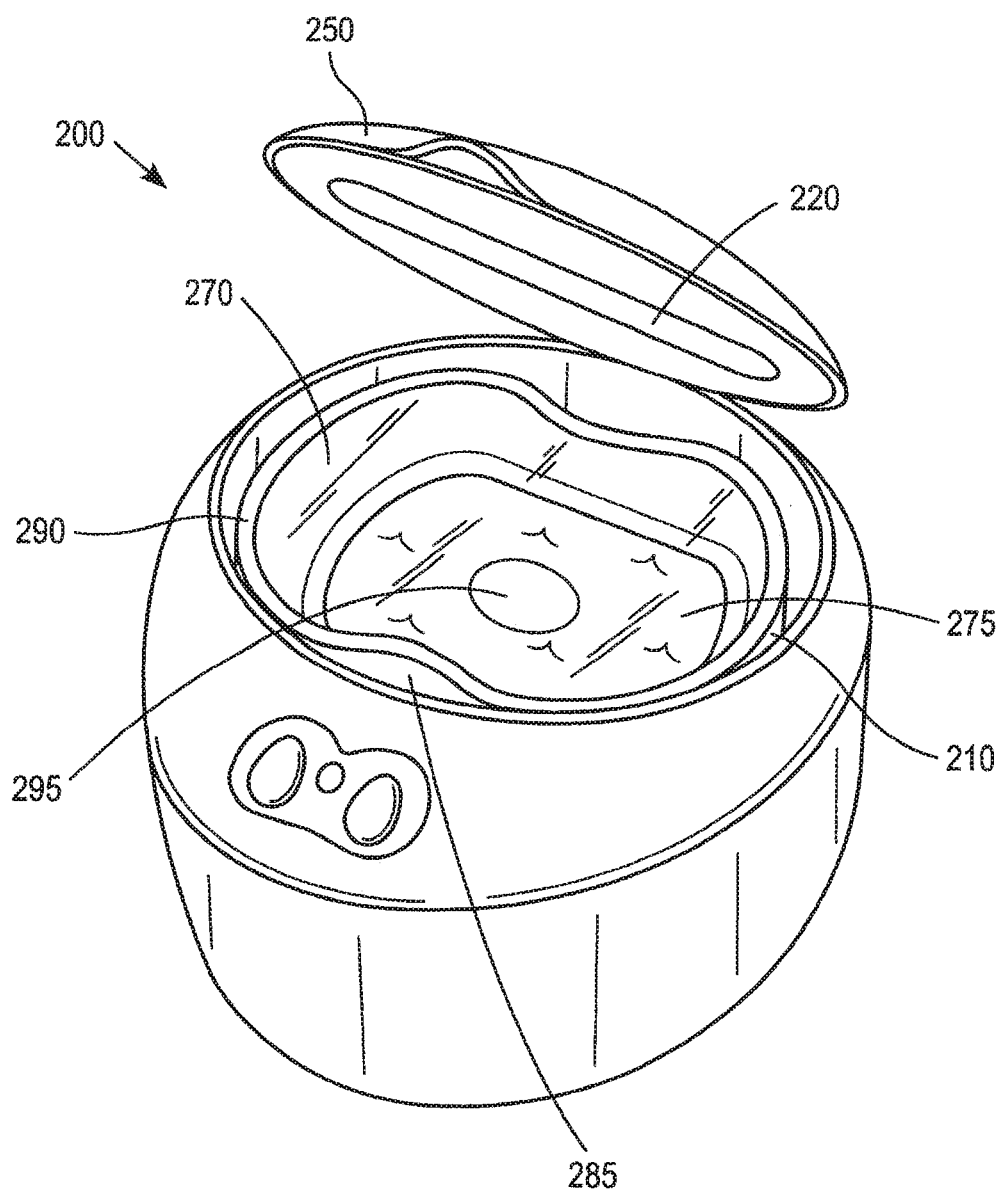
FIG. (1c)

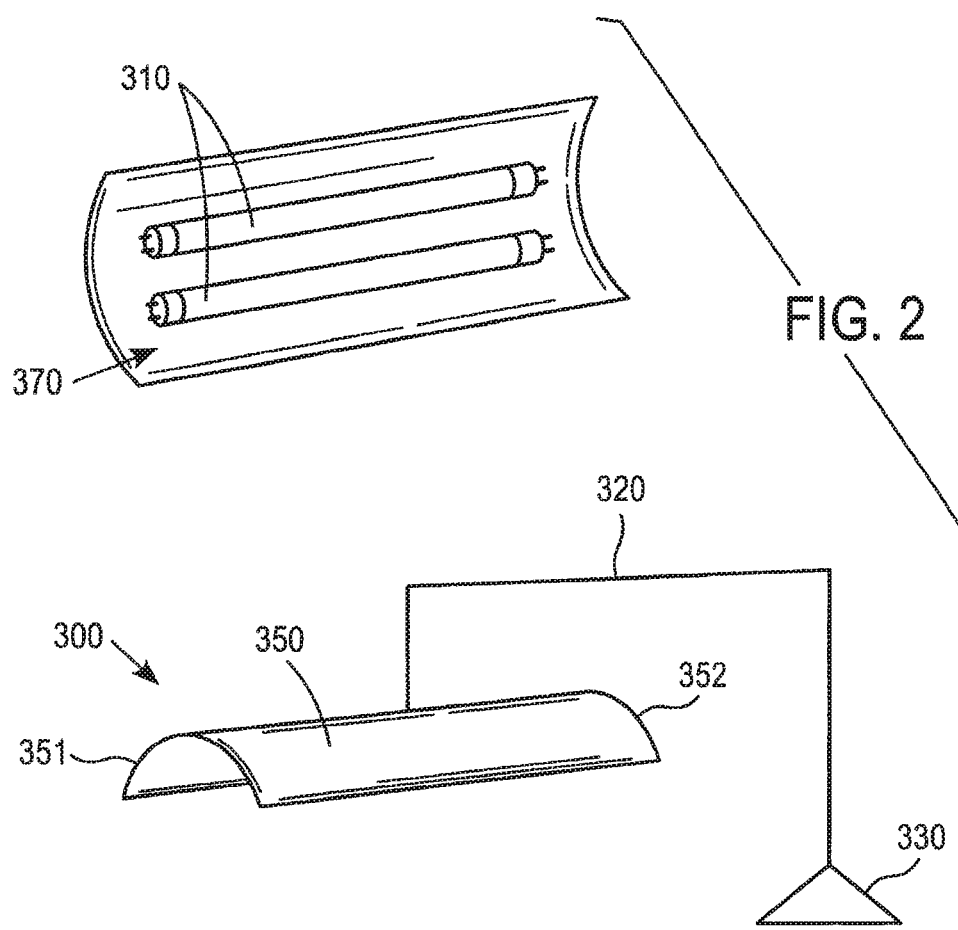

DEVICE AND METHOD FOR STERILIZATION OF INSTRUMENTS AND SURFACES

PRIORITY

The present application is a divisional of U.S. application Ser. No. 13/839,011, filed on 15 Mar. 2013, which claims the benefit of U.S. Provisional Application No. 61/722,597, filed on Nov. 5, 2012. The entire contents of each of U.S. application Ser. No. 13/839,011 and U.S. Provisional Application No. 61/722,597 are hereby incorporated herein by reference in its entirety.

BACKGROUND

Contamination of surfaces with infectious microorganisms such as HIV, hepatitis and other viruses and bacteria presents a serious health hazard. Screening procedures may miss contaminants, and known sterilization procedures may not effectively inactivate all infectious viruses and other microorganisms.

Generally, medical instruments are sterilized by using heat, steam, chemicals and/or a combination of these. In some instances, for example, these approaches cause damage to the instrument. Alternatively, if these approaches are only used for only brief exposure, these approaches may not be very effective in sterilizing.

Alternative sterilization efforts may not be sufficient or are overly burdensome. For example, alcohol may be used to clean tonometers. However, alcohol has limited effect with diseases such as adenoviruses. Ocular lenses, which are often used by ophthalmologists in the operating rooms and in the office to examine the eye, may be cleaned by a system which uses gluteraldehyde (CIDEX). However, this requires extensive washing to remove the agent and ten hours for complete treatment.

Ultraviolet light alone can kill some pathogens but, in the absence of a photoactivatable substance, this reaction may not be sufficient. Basic instruments using UV or blue light are used for cleaning false teeth or toothbrushes, as well as treating acne, are well known in the art. In this regard, these instruments have inadequate overall light exposure to decontaminate all surfaces or all pathogens. Furthermore, while UV light, used alone, is known to cause nucleic acid damage to cells, exposure to UV light alone also causes up-regulation of cellular repair mechanisms. In the literature it has been reported that viruses inactivated by UV light alone will reactivate a small percentage of the time due to up-regulation of the host cell's nucleic acid repair mechanisms (see U.S. Pat. No. 7,901,673).

Combined exposure to a photoactivatable substance and a photoactivator has been shown to effectively inactivate a wide range of pathogens in blood. Solvent detergent methods of blood component decontamination work by dissolving phospholipid membranes surrounding viruses such as HIV, and may cause some alterations to plasma proteins. See, Rock, G., et al. (2010), "A comparison of methods of pathogen inactivation of FFP," Vox Sanguinis 2010, 100, 1-10.

The use of photoactivatable substances, compounds which absorb light of a defined wavelength and transfer the absorbed energy to an energy acceptor, has been proposed for sterilization (see European Patent application 0 196 515). The use of non-endogenous photoactivatable substances such as porphyrins, psoralens, acridine, toluidines, flavine (acriflavine hydrochloride), phenothiazine derivatives, and dyes such as neutral red, and methylene blue, as blood additives is suggested. Protoporphyrin, which occurs naturally within the body, can be metabolized to form a photo-activatable substance; however, its usefulness is limited in that it degrades desired biological activities of proteins. Chlorpromazine is also exemplified as one such photoactivatable substance; however its usefulness is limited by the fact that it should be removed from any fluid administered to a patient after the decontamination procedure because it has a sedative effect.

Goodrich, R. P., et al. (1997), "The Design and Development of Selective, Photoactivated Drugs for Sterilization of Blood Products," Drugs of the Future 22:159-171, provides a review of some photoactivatable substances including psoralens, and some of the issues of importance in choosing photoactivatable substances for decontamination of blood products. The use of texaphyrins for DNA photo-cleavage is described in U.S. Pat. Nos. 5,607,924 and 5,714,328. The use of sapphyrins for viral deactivation is described in U.S. Pat. No. 5,041,078. Inactivation of extracellular enveloped viruses in blood and blood components by Phenthiazin-5-ium dyes plus light is described in U.S. Pat. No. 5,545,516. The use of porphyrins, hematoporphyrins, and merocyanine dyes as photoactivatable substance agents for eradicating infectious contaminants such as viruses and protozoa from body tissues such as body fluids is disclosed in U.S. Pat. No. 4,915,683 and related U.S. Pat. No. 5,304,113.

The reactivity of psoralen derivatives with viruses has been studied. See, Hearst and Thiry (1977) Nuc. Acids Res. 4:1339-1347; and Talib and Banerjee (1982) Virology 118: 430-438. U.S. Pat. No. 4,124,598 suggests the use of psoralen derivatives to inactivate RNA viruses. U.S. Pat. No. 4,169,204 suggests that psoralens may provide a means for inactivating viruses for the purpose of vaccine production but presents no experimental support for this proposition. European patent application 0 066 886 teaches the use of psoralen inactivated cells, such as virus-infected mammalian cells, for use as immunological reagents and vaccines. Hanson (1983) in: Medical Virology II, de la Maza and Peterson, eds., Elsevier Biomedical, New York, pp. 45-79, reports studies which have suggested that oxidative photo-reactions between psoralens and proteins may occur. U.S. Pat. Nos. 4,693,981 and 5,106,619 disclose the use of psoralens to prepare inactivated viral vaccines. These patents disclose preparing vaccines by treating viruses with furocoumarins and long wavelength UV light for a time period sufficiently long enough to render the virus non-infectious but less than that which may result in degradation of its antigenic characteristics under conditions which limit the availability of oxygen and other oxidizing species. U.S. Pat. No. 4,402,318 discloses a method of producing a vaccine by adding methylene blue and exposing the vaccine to light and an electric field concurrently to completely inactivate the viruses, bacteria, cells and toxins. U.S. Pat. No. 6,165,711 discloses a process for disintegrating nucleic acids to make vaccines by exposing biologically active material to phenothiazine and a laser beam.

The mechanism of action of psoralens is described as involving preferential binding to domains in lipid bilayers, e.g. on enveloped viruses and some virus infected cells. Photoexcitation of membrane-bound agent molecules leads to the formation of reactive oxygen species such as singlet oxygen which causes lipid peroxidation. A problem with the use of psoralens is that they attack cell membranes of desirable components of fluids to be decontaminated, such as red blood cells, and the singlet oxygen produced during the reaction also attacks desired protein components of fluids being treated.

U.S. Pat. No. 4,727,027 discloses the use of furocoumarins including psoralen and derivatives for decontamination of blood and blood products, but teaches that steps must be taken to reduce the availability of dissolved oxygen and other reactive species in order to inhibit denaturation of biologically active proteins. Photoinactivation of viral and bacterial blood contaminants using halogenated coumarins is described in U.S. Pat. No. 5,516,629, U.S. Pat. No. 5,587,490 and U.S. Pat. No. 5,418,130 disclose the use of substituted psoralens for inactivation of viral and bacterial blood contaminants. The latter patent also teaches the necessity of controlling free radical damage to other blood components. U.S. Pat. No. 5,654,443 teaches new psoralen compositions used for photodecontamination of blood. U.S. Pat. No. 5,709,991 teaches the use of psoralen for photodecontamination of platelet preparations and removal of psoralen afterward. U.S. Pat. No. 5,120,649 and related U.S. Pat. No. 5,232,844 disclose the need for the use of "quenchers" in combination with photoactivatable substances which attack lipid membranes, and U.S. Pat. No. 5,360,734 addresses this problem of prevention of damage to other blood components.

Photoactivatable substances which attack nucleic acids are known to the art. U.S. Pat. No. 5,342,752 discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. U.S. Pat. No. 5,798,238 discloses the use of quinolone and quinolone compounds for inactivation of viral and bacterial contaminants.

Binding of DNA with photoactive agents has been exploited in processes to reduce lymphocytic populations in blood as taught in U.S. Pat. No. 4,612,007 and related U.S. Pat. No. 4,683,889.

Riboflavin (7,8-dimethyl-10-ribityl isoalloxazine) has been reported to attack nucleic acids. U.S. Pat. Nos. 6,258,577 and 6,277,337 disclose the use of riboflavin and light to inactivate microorganisms which may be contained in blood or blood products. U.S. Pat. No. 6,268,120 discloses riboflavin derivatives which may be used to inactivate microorganisms. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360-363; and Speck, W. T. et al. (1976), "Further Observations on the Photooxidation of DNA in the Presence of Riboflavin," Biochim Biophys Acta 435:39-44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207-217. Hoffmann, M. E., et al. (1979), "DNA Strand Breaks in Mammalian Cells Exposed to Light in the Presence of Riboflavin and Tryptophan," Photochemistry and Photobiology 29:299-303 describes the use of riboflavin and tryptophan to induce breaks in DNA of mammalian cells after exposure to visible fluorescent light or near-ultraviolet light. The article states that these effects did not occur if either riboflavin or tryptophan was omitted from the medium. DNA strand breaks upon exposure to proflavine and light are reported in Piette, J. et al. (1979), "Production of Breaks in Single- and Double Stranded Forms of Bacteriophage phi X174 DNA by Proflavine and Light Treatment," Photochemistry and Photobiology 30:369-378, and alteration of guanine residues during proflavine-mediated photosensitization of DNA is discussed in Piette, J., et al. (1981), "Alteration of Guanine Residues during Proflavine Mediated Photosensitization of DNA," Photochemistry and Photobiology 33:325-333. J. Cadet, et al. (1983), "Mechanisms and Products of Photosensitized Degradation of Nucleic Acids and Related Model Compounds," Israel J. Chem. 23:420-429, discusses the mechanism of action by production of singlet oxygen of rose bengal, methylene blue, thionine and other dyes, compared with mechanisms not involving production of singlet oxygen by which nucleic acid attack by flavin or pteron derivatives proceeds. Riboflavin is exemplified in this disclosure as having the ability to degrade nucleic acids. Korycka-Dahl, M., et al. (1980), "Photodegradation of DNA with Fluorescent Light in the Presence of Riboflavin, and Photoprotection by Flavin Triplet-State Quenchers," Biochimica et Biophysica Acta 610:229-234 also discloses that active oxygen species are not directly involved in DNA scission by riboflavin. Peak, J. G., et al. (1984), "DNA Breakage Caused by 334-nm Ultraviolet Light is Enhanced by Naturally Occurring Nucleic Acid Components and Nucleotide Coenzymes," Photochemistry and Photobiology 39:713-716 further explores the mechanism of action of riboflavin and other photosensitizers. However, no suggestion is made that such photoactivatable substances be used for decontamination according to embodiments of the devices and methods described herein.

All publications referred to herein are hereby incorporated by reference to the extent not inconsistent herewith.

SUMMARY

An embodiment may be a device for decontaminating a medical device, the device may include: a compartment adapted to contain a medical device and a solution, the solution may include a photoactivatable substance; and a light system providing 360 degrees of exposure to the compartment. The compartment may provide an enclosure for the entire medical device contained therein. The compartment may include holding devices for holding a container, such as a bag or cup. The holding devices may be hooks or loops. The compartment may include multiple light sources. The compartment may have a reflective coating on some of (e.g., at least 25%), most of (e.g., at least 65%), or essentially the entire (e.g., at least 90%) surface of the compartment. The device may further include a container, the container adapted to be placed in the compartment. The container may be a bag system. The bag system may include a bag adapted to contain the medical device and solution, wherein the bag may include a seal and an input device for inputting and/or draining the solution. The seal may be essentially permanent, wherein the bag and/or seal is destroyed by breaking the seal to recover the object. Alternatively, the seal may be resealable. The input device may include a valve to control when the input device is open or closed. The light system may provide UV light.

An embodiment may be a method for decontaminating a medical device, the method may include: placing a medical device in a compartment with a solution, the solution may include a photoactivatable substance; incubating the medical device in the solution to allow the photoactivatable substance to attach to pathogens; and exposing the compartment to 360 degrees of light exposure to activate the photoactivatable substance. The method may further include placing the medical device and solution in a container, and placing the container in the compartment. The method may include: placing the medical device in a bag and adding solution via an input device with a valve; and after exposing to light, draining the solution via the input device. The light may be UV light. The photoactivatable substance may be riboflavin with or without tryptophan.

An embodiment may be a device for decontaminating a surface, the device may include: a concave piece adapted to surround a surface; and a light system providing 180 degrees of exposure to the surface. Essentially the entire surface-surrounding side of the concave piece may have a reflective coating.

An embodiment may be a method for decontaminating a surface, the method may include: applying a solution with a photoactivatable substance to the surface; exposing the surface to 180 degrees of light exposure to activate the photoactivatable substance. The solution may be allowed to contact the surface for a sufficient period of time. The surface may be skin. The skin may include a wound or a proposed surgical incision site.

An embodiment may be a device for introducing light into a nasal cavity, the device may include: a handle containing a power source; a light source; and a flexible arm connecting the handle and the light source, the light source providing about 360 degrees of UV light.

An embodiment may be a method for disinfecting a nasal passage, the method may include: applying a solution to a nasal passage, the solution may include a photoactivatable substance; exposing the nasal passage to 360 degrees of light exposure to activate the photoactivatable substance.

An embodiment may be a method for treating skin, the method may include adhering a skin perfusion chamber to the skin, applying a solution to the skin, the solution may include a photoactivatable substance; exposing the skin to light to activate the photoactivatable substance.

BRIEF DESCRIPTION OF THE SEVERAL VIEWS OF THE DRAWINGS

The invention can be better understood with reference to the following drawings. The components of the drawings are not necessarily to scale, emphasis instead being placed upon clearly illustrating the principles of embodiments the present invention.

FIG. 1c shows an exemplary device, which includes a container in the form of a cup.

FIG. 2 shows an exemplary device adapted to provide a 180 degrees exposure of light to an object, such as a surface or a wound.

DETAILED DESCRIPTION OF PREFERRED EMBODIMENTS

Figure 1A:
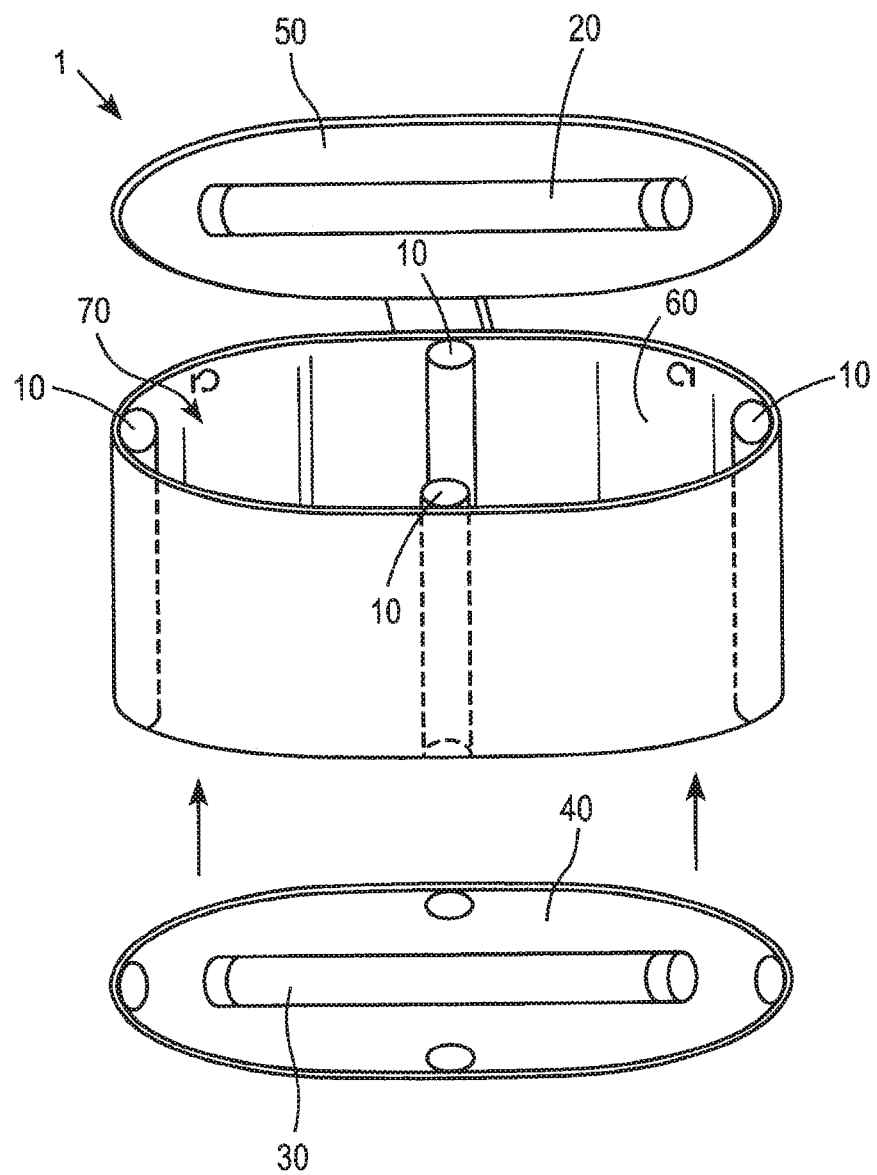
FIG. 1a shows an exemplary device, the device including an exemplary compartment.

An embodiment relates to a device and method which permits inactivation of pathogens on surfaces.

Exemplary pathogens include viruses (both extracellular and intracellular), bacteria, bacteriophages, fungi, blood-transmitted parasites, and protozoa. Exemplary viruses include adenovirus, human immunodeficiency virus (HIV), hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Exemplary bacteria include *P. aeruginosa, S. aureus, S. epidermis, L. monocytogenes, E. coli, K. pneumonia* and *S. marcescens*. Exemplary bacteriophages include phi X174, phi 6, lambda, R17, $T_4$, and $T_2$.

An embodiment relates to a device with a light source (visible, UV, black, or other) with a compartment for surrounding an object to be treated. Upon activation of the light source, the compartment is exposed to light (visible, UV, black, or other).

An embodiment relates to a method and device to inactivate pathogens on specific objects and/or solid surfaces using a photoactivatable compound and a photoactivator in the form of a light source.

An embodiment relates to a method and device to sterilize an object with several surfaces, including medical instruments, such as a tonometer or an optical lens.

An embodiment relates to a method and device in which the object is placed in a container which has or will have introduced into it a solution containing a photoactivatable substance. Following exposure to the substance, photoactivation will occur to inactivate pathogens. Preferred in this embodiment are surround lights and reflective surfaces, which achieve a 360 degree exposure to the photoactivation, ensuring that all surfaces are treated.

Compartment

The compartment may provide a complete enclosure for the object to be treated. For example, the entire object may fit with the compartment. For example, all surfaces of the object may be within the compartment and all surfaces may be treated. The compartment may provide an enclosure for essentially all of an object to be treated, with the possible exception of a bottom side of the object. The object and solution may be placed directly in the compartment, or the object and solution may be placed in a container, the container being placed in the compartment. The compartment allows sterilization of medical instruments and other 3-D objects.

The compartment may be designed to directly hold an object and a solution containing a photoactivatable substance. The compartment may be designed to hold a container, the container directly holding an object and a solution containing a photoactivatable substance. For example, the compartment may have an interior space adapted to hold a container, where the container is the same size or a smaller size than the interior space. The compartment may hold the container by a holding device. For example, the holding device may be a lip or ring at the top of the interior space, hooks, loops or clips.

The container may be composed of a material which permits light permeation, for example at the wave length of the light source. The container may be of a plastic material.

The container may be disposable. For example, a disposable bag which contains a solution into which an object is placed for inactivation of contaminating pathogens. The bag may be essentially permanently sealable (wherein the bag and/or seal is destroyed by breaking the seal to recover the object) and/or resealable. For example, a reusable and/or disposable cup may be used.

The container may be any system which may allow for drainage of the photoactivatable solution with the potential for storage of the solution until required. The container may be in the form of any container including an enclosed bag system, as exemplarily depicted in FIG. 4. The container may be a bag, such as an interconnected bag system which allows introduction of an object and introduction of the photoactivatable solution. Following activation, the solution can be drained and the sterilized object stored for future use. The container may be in the form of a cup, as exemplarily depicted in FIG. 5. The container may be a cup-like structure which is open on the top to allow introduction of the object, the solution, and exposure to light, which may be 360 degree exposure to light. Both the bag and cup may be permeable to the light source. For example, at least 50% of the irradiation, at a mean wavelength, or at least 70% of the irradiation, at a mean wavelength, at least 90% of the irradiation, at a mean wavelength, can pass through the container.

An embodiment is a method to treat a one dimensional area such as a superficial ulcer or other contaminated region which may be either animate or inanimate. In this embodiment, the surface could be immersed in the liquid through use of a specially adapted chamber, perfused with the liquid or sprayed with it to a point which achieves a sufficient dose of the photoactivatable agent to bind all pathogenic nucleic acids. After an incubation period, photoactivation occurs.

In an embodiment, a device may include a perfusion chamber. An exemplary perfusion chamber may be a plastic or other cylinder-like structure which is open on both ends. One end may be affixed, such as through an adhesive, such as glue, to the surface of a contaminated site and solution may then be added to the chamber to allow incubation with a photoactivatable substance prior to light exposure.

Exemplary applications include treatment of infected lesions and ulcers. Exemplary applications also include providing prophylaxis in a pre-surgical treatment of a proposed incision site to reduce the number of pathogens on the surface of the skin before surgery. Exemplary applications include use in dermatology and immunology to look at cell migration and allow treatment of an ulcer on the skin with full saturating treatment of any pathogens in the ulcer.

An exemplary method to allow contact with the solution and a single surface, for example a wound or an ulcer, is to spray the surface with the solution or allow the solution to drip onto the surface until saturation of the nucleic acid binding sites has occurred, followed by light exposure.

In an exemplary embodiment, the surface is located on an animal. For example, the surface may be located on the skin of a human. For example, the surface may be a wound of an animal, such as a human. For example, the surface may be an infected ulcer, such as an external ulcer. For example, the surface may include a proposed surgical incision site.

An embodiment is the use of the method to inactivate pathogens carried in nasal passages. Pathogens carried in the nasal passages cause problems, for example in hospitals, as they transmit infection. Upon admission to a hospital, an individual could have their nasal passages soaked in the solution either by immersion or by spraying or swabbing the solution into the nasal passages. A small light source could then be introduced into the nostrils to inactivate the pathogens. Disposable plastic covers could be used on the light(s), which may be located, for example, centrally, in the nasal passages with the infected area surrounding the light(s).

It is also envisioned that embodiments may be used in food preparation, such as the surfaces of fruit, and in veterinarian work.

Light

The light source may be sufficient to ensure exposure of the entire surfaces (all sides) of the object. For multi-surface objects, such as a tonometer, the device may have a light source on multiple sides in order to provide essentially 360 degrees of exposure. For a single-surface object or one with several planes, such as a surface ulcer, the light source may provide 180 degrees of exposure. An exemplary light source may be a single source, direct light, such as a flashlight. An embodiment of a device may include a semicircular curved holder with a light reflective interior and two or more lights in order to provide, preferably, 180 degrees of exposure.

Figure 1B:
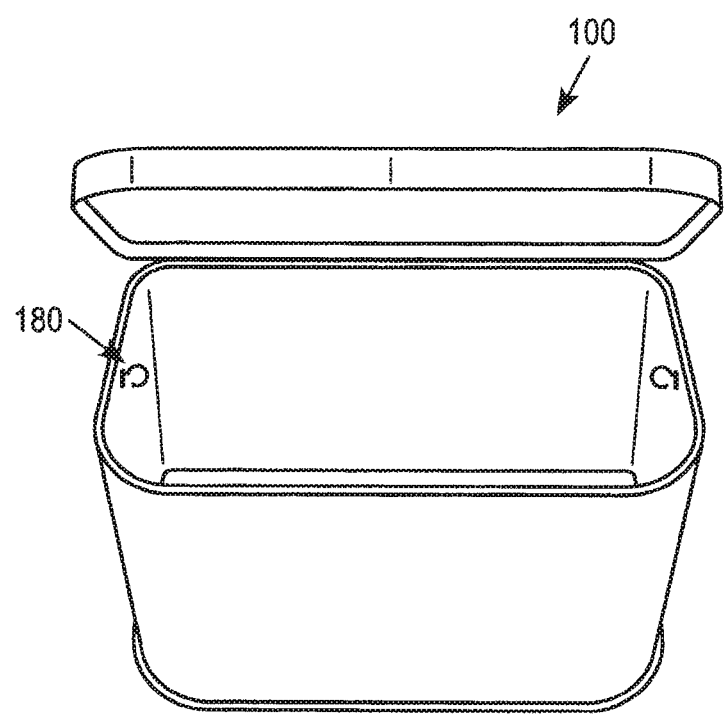
FIG. 1b shows an exemplary device in the shape of a rectangular prism, with rounded edges.
Figure 3:
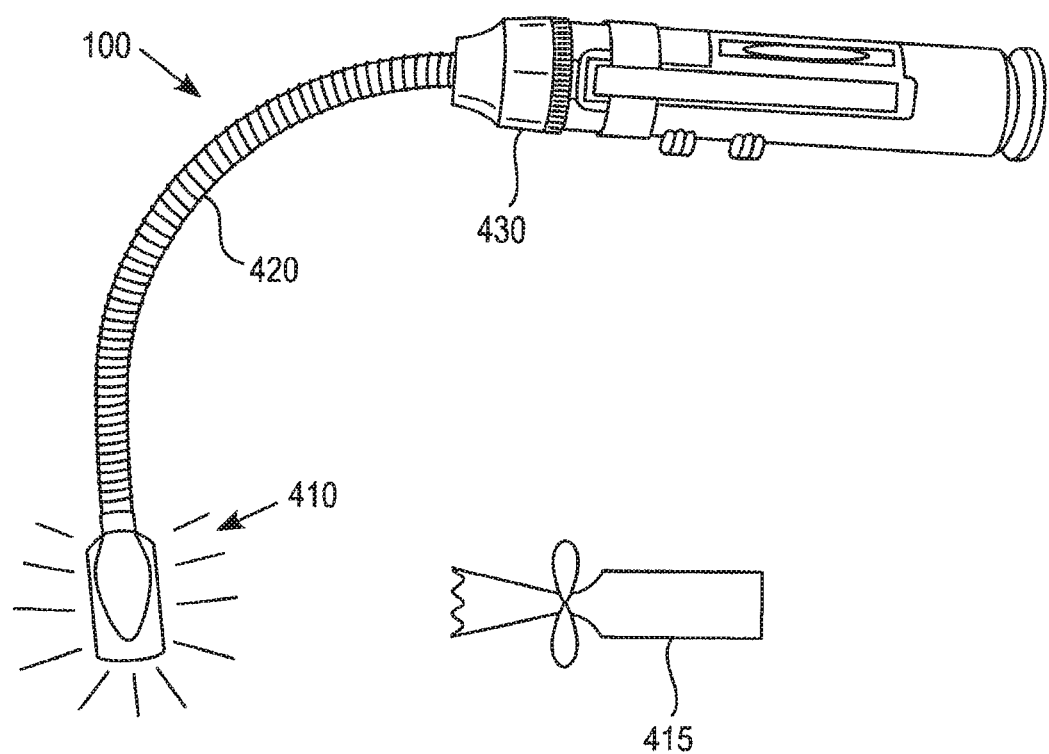
FIG. 3 shows an exemplary device adapted to introduce light into a cavity, such as a body cavity, such as the nose.

The light source may ensure total exposure for activation. Three exemplary configurations of the light source include the following: (1) a 360 degree light source with optional amplifiers and optional reflective material (an embodiment is depicted in FIGS. 1a-c); (2) a concave 180 degree light source with optional amplifiers and optional reflective material (an embodiment is depicted in FIG. 2); and (3) a small light source located on a flexible base with optional disposable covers on the light source which is introduced into body cavities, such as the nose (an embodiment is depicted in FIG. 3). Complete (360°) light exposure is appropriate when the target is a 3-dimensional object, while when the target is relatively flat surface, 180 degree exposure is appropriate and for specific areas such as nasal passages a central light source is appropriate.

The device may also include reflective material to provide greater exposure of light in the compartment. The reflectors may be a reflective coating on the compartment, reflective dots on part of the compartment, or other. The compartment may be made of a reflective material.

In an embodiment, wavelengths in the ultraviolet to visible range may be used. For example, the light source or sources may provide light in the visible range, light in the ultraviolet range, or may be a mixture of light in the visible and ultraviolet ranges. For example, a light source may be a fluorescent or luminescent source providing light of about 300 nm to about 700 nm, and for example about 320 nm to about 447 nm of radiation. Ultraviolet light in the range of about 373 has been shown to provide optimal activation of riboflavin. An appropriate wavelength to activate the photoactivatable substance may be used. The wavelength used will depend on the photoactivatable substance selected, as is known to the art or readily determinable without undue experimentation following the teachings hereof.

A sufficient amount of photoirradiation to activate the photoactivatable substance may be used. For example, 1 to 30 J/cm$^2$ may be used.

A light source may be a light tube/bulb or a LED light strip. For example, LED UV lights which are on a silicon flexible base may be used. Exemplary LED UV lights may be in strings and may be 12 amps and up. A wrap, for example in a circle or spiral or other pattern, of LED UV lights may be used in the compartment to provide a 360 degree illumination source. In an embodiment, the light source includes an ability to determine whether the light is still optimally functional, e.g., providing an indication of the percentage decrease in light intensity that the lights are providing over time.

Solution

A solution may contain a photoactivatable substance in solution with a fluid carrier. The activated photoactivatable substance may be capable of inactivating infectious particles present, such as by interfering to prevent their replication. In embodiments, the photoactivatable substance may bind with the nucleic acid of any pathogens adherent to the object. Following binding, the substance is activated by photoactivation (radiation) via the light source to effectively kill the pathogens. Specificity of action of the photoactivatable substance is conferred by the close proximity of the photoactivatable substance to the nucleic acid of the particle and this may result from binding of the photoactivatable substance to the nucleic acid. "Nucleic acid" includes ribonucleic acid (RNA) and deoxyribonucleic acid (DNA). Other photoactivatable substances may act by binding to cell membranes or by other mechanisms.

In embodiments, the object may be exposed to the solution to allow the photoactivatable substance to bind with the nucleic acid of any pathogens adherent to the object. For example, the object may be exposed for at least 10-20 minutes prior to photoactivation.

The solution may bathe the object. For example, the object, concurrent with or prior to exposure to light, may be exposed to a photoactivatable substance. The solution may be applied on the object in the compartment or in a container. The object in solution may be mixed, shaken or stirred to obtain greater coverage of the solution on all surfaces of the object. The solution may also be sprayed onto the object, such as a wound or intranasally. In an embodiment, a volume of solution sufficient to entirely subsume the object in a bath of solution may be used. For example, 5-10 mL of solution may be used for a lens. The amount of solution may vary depending on the object. In an embodiment, the amount of solution is enough to completely cover the object. In an embodiment, the amount of photoactivatable substance to be contacted with the surface will be an amount sufficient to adequately inactivate the reproductive ability of an infectious particle.

Optimal concentrations for desired photoactivatable substances may be readily determined by those skilled in the art without undue experimentation. Preferably the photoactivatable substance is used in a concentration of at least about 1 uM up to the solubility of the photoactivatable substance in the fluid, and preferably about 10 uM. For 7,8-dimethyl-10-ribityl isoalloxazine a concentration range between about 1 uM and about 160 uM is preferred, preferably about 10 uM.

The photoactivatable substance may be any photoactivatable substances known in the art to be useful for inactivating microorganisms or other infectious particles. A "photoactivatable substance" is defined as any compound which absorbs radiation of one or more defined wavelengths and subsequently utilizes the absorbed energy to carry out a chemical process. Examples of such photoactivatable substances include porphyrins, psoralens, dyes such as neutral red, methylene blue, acridine, toluidines, flavine (acriflavine hydrochloride) and phenothiazine derivatives, coumarins, quinolones, quinones, and anthroquinones. Photoactivatable substances useful may include compounds which adsorb to nucleic acids, thus focusing their photodynamic effect upon microorganisms and viruses with little or no effect upon accompanying cells or proteins. Other photoactivatable substances are also useful in this device, such as those using singlet oxygen-dependent mechanisms. Additional photoactivatable substances are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photoactivatable substances include synthetically derived analogs and homologs of endogenous photoactivatable substances which may have or lack lower (1-5) alkyl or halogen substituents of the photoactivatable substances from which they are derived, and which preserve the function and substantial nontoxicity thereof. A preferred embodiment is when the photoactivatable substances are riboflavin, a psoralen, or methylene blue. Most preferred is when the photoactivatable substance is riboflavin.

In an embodiment, the solution may be composed of a 1% solution of riboflavin (vitamin B2).

In an embodiment, the solution is discarded at the end of the process of sterilization of an object.

In embodiments, the solution does not have to be at a physiological pH, i.e., the solution does not require a buffer.

The solution includes a fluid carrier. The fluid carrier may be water or any of a number of salt or other solutions.

Object to be Treated

The object to be treated may be an object with multiple surfaces, such as occurs with medical instruments. In an embodiment, the medical instrument is a tonometer. In an embodiment, the medical instrument is an ocular lens. All surfaces of a three dimensional object may be treated.

The object to be treated may be a wound, such as wound on a skin surface. The object to be treated may be an infected lesions and ulcers. The object to be treated may be a proposed surgical incision site. These may be on humans or animals. All surfaces of a wound may be treated.

The object to be treated may be a large surface, for example an essentially flat surface, wherein only a part of the surface is to be treated.

The object to be treated may be the nasal passages or eye cavity. All surfaces of an extended section of nasal passage may be treated.

The object to be treated may be food, such as surfaces of fruit and/or vegetables. All exterior surfaces of the food may be treated.

EMBODIMENTS

FIG. 1a shows an exemplary device 1. The device 1 includes a compartment 70. The compartment 70 includes a top 50, sides 60 and a bottom 40. The compartment 70 may provide a complete enclosure for any object placed therein. The top 50 may be removable from the device, or at least partially removable, for example by a hinge, from the device. The sides 60 and bottom 40 may be integrally formed. The sides 60 may be of any shape, such as a circle, oval, square, rectangle, etc.

The compartment 70 may be of sufficient size to allow adequate containment of the object while permitting adequate exposure for photoactivation. For an optical lens, a preferable compartment may hold 5-10 ml of solution, but the volume will depend on the size of the object to be treated.

The compartment 70 includes holding devices 80, which may be hooks or loops. The holding devices 80 hold a container, such as a bag or a cup in the compartment 70.

The compartment 70 includes multiple light sources 10, 20, 30 which may be on the sides, top and bottom of the compartment. The compartment 70 may include a reflective coating on some of (e.g., at least 25%), most of (e.g., at least 65%), or essentially the entire (e.g., at least 90%) surface of the compartment 70 to ensure complete 360 degrees of light exposure to an object therein. This allows exposure of all or essentially all surfaces of the object to the solution.

Following incubation to allow the photoactivatable substance to attach to any nucleic acid present, the compartment may be exposed to light to activate the photoactivatable substance. For a multi-sided instrument this may be accomplished by having a light source capable of delivering a 360 degree exposure. Following treatment, the container (if present) and object may be removed from the compartment 70, the solution removed, and the article stored. If an enclosed bag system is used, this permits long-term storage of the instrument until use. An open compartment or container system allows immediate removal of the device and use.

In embodiments an object, e.g., a lens, a tonometer, or other instrument, and a solution with a photoactivatable substance are inserted into a container. The container (with an object and solution) is then inserted into the compartment 70, the light sources 10, 20, 30 are turned on, and any pathogens are exposed to the combined effects of a photoactivatable substance and light. For example, photoactivatable substance such as riboflavin will intercalate into the nucleic acid of pathogens. Subsequently, exposure to UV light will result in disruption of the pathogen and an inability of the pathogen to replicate. This may result in the inactivation of a broad range of pathogens including, but not limited to, HIV, Hepatitis B, Adenovirus, West Nile Virus, and *E. coli*.

In an exemplary method, a solution with a photoactivatable substance may be applied into a container, such as a bag or a cup. An object is added to the container either before, after or during addition of the solution. The solution is allowed to contact the object for a sufficient period of time. The container is inserted into the compartment 70, before or after any of the above steps. The top 50 of the device is closed and the device is powered to provide light into the compartment to activate the photoactivatable substance. The light may be delivered in a manner to provide 360 degrees of light exposure to the object, for example to all sides and surfaces of the object. This may effectively kill pathogens on the object.

FIG. 1b shows an exemplary device 100 in the shape of a rectangular prism, with rounded edges. The device 100 includes light sources on all six interior sides. All six interior sides have a reflective coating or are made of a reflective material. In embodiments, only certain interior surfaces may have a reflective coating or be made of reflective material. The device 100 may also include holding devices 180, for holding a container, such as a bag or cup.

FIG. 1c shows an exemplary device 200. The device 200 includes a container 290 in the form of a cup. The container 290 is shown containing an object 295 to be treated and a solution 275 with a photoactivatable substance. The container 290 includes a concave portion 285 that is spaced from the compartment 270 to allow easy withdrawal of the container 290 from the compartment 270. The device 200 has a hinged top 250 that can be opened to withdraw the container 290 from the compartment 270 of the device after photoactivation. The top 250 includes a light source 220.

FIG. 2 shows an exemplary device 300. The device 300 is adapted to provide a 180 degrees exposure of light to an object, such as a surface or a wound. The device 300 includes a concave piece 350 that may hang from an adjustable arm 320 on a base 330. The interior (exposure) surface 370 of the concave piece 350 includes one or more light sources 310. The interior surface 370 may include optional amplifiers and an optional reflective material. The ends 351,352 of the concave piece 350 may be open or may include enclosing pieces of material (not shown) in order to form a cavity.

In embodiments, the concave piece 350 may be shaped differently, such as flat or be a circular light source, as in a flashlight In an exemplary method, a solution with a photoactivatable substance may be applied onto an object, such as a surface or a wound. The solution is allowed to contact the object for a sufficient period of time. The interior surface 370 of the concave piece 350 is applied to the object. The object may be moved to the concave piece 350 and/or the concave piece 350 may be moved to the object. The device 300 is powered to provide light onto the object to activate the photoactivatable substance. The light may be delivered in a manner to provide 180 degrees of light exposure to the object, for example to all sides and surfaces of the object, except the bottom surface. This may effectively kill pathogens on the object.

FIG. 3 shows an exemplary device 400. The device 400 is adapted to introduce light into a cavity, such as a body cavity, such as the nose. For example, the cavity acts as the compartment and the inner surface of the cavity is the object to be treated. A solution with a photoactivatable substance may be applied, such as by squirting or spraying, onto a cavity, such as the inner surface of the cavity.

The device 400 includes a piece 430 which acts as a handle and may contain a power source, such as a battery. A flexible arm 420 connects from the piece 430 to a light source 410. A disposable cover 415 may be applied over the light source for introduction of the light source 410 into the cavity to be treated.

In an exemplary method, a solution with a photoactivatable substance may be applied, such as by squirting or spraying, into a cavity, such as a body cavity, such as the nose or eye socket. The solution is allowed to contact the cavity for a sufficient period of time. Then, the light source 410 is inserted into or next to the cavity and powered to provide light into the cavity to activate the photoactivatable substance. This may effectively kill pathogens in the cavity.

Figure 4:
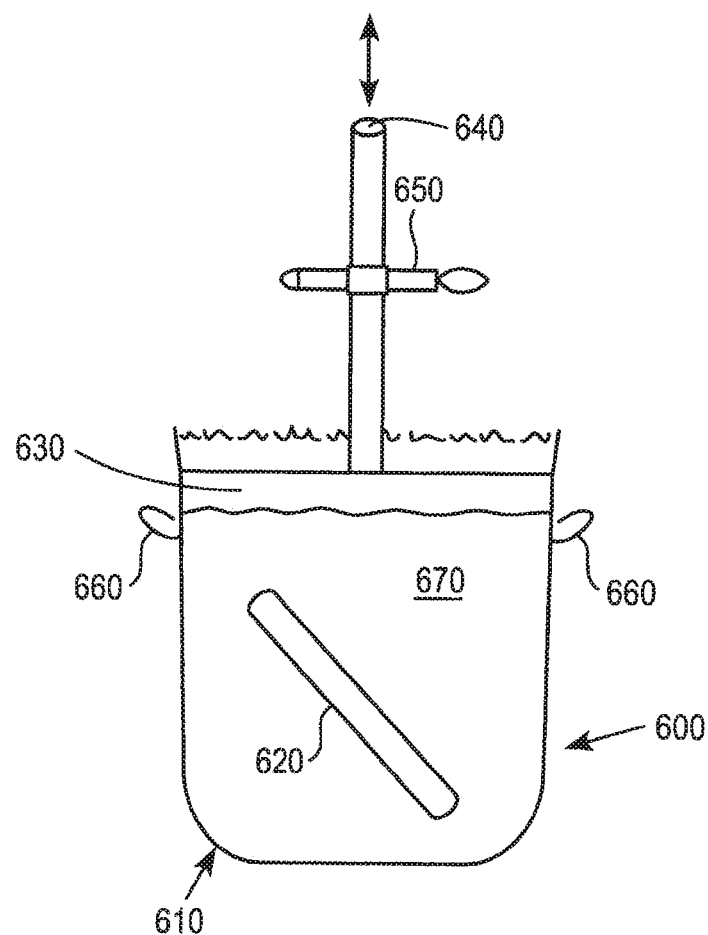
FIG. 4 shows an exemplary container in the form of a bag system.

FIG. 4 shows an exemplary container 600. The container 600 may be a bag system. The container 600 may include a bag 610. The bag 610 may be plastic. The bag 610 is adapted to hold a solution 670 and an object 620 to be treated. The bag 610 may be disposable. The bag 610 may include a holding device 660, such as hooks or loops. The bag 610 may have a seal 630. The seal 630 may be essentially permanent (wherein the bag is destroyed by breaking the seal 630 to recover the object), such as from an adhesive or a welding. The seal 630 may be resealable, such as from a zip-lock seal. The bag 610 may have an input device 640 for inputting and/or drainage of the solution 670. The input device 640 may be a tube. The input device 640 may include a valve 650 to control when the input device 640 is open or closed.

In an exemplary method, an object 620 is added to a container 600, in a bag 610. The bag 610 is sealed with a seal 630. A solution 670 may be added to the bag 610 via an input device 640 while a valve 650 is open. The solution is allowed to contact the object 620 for a sufficient period of time. The container 600, with or without the input device 640, is applied to a compartment, such as compartment 70 in Figure la. Light is applied to the compartment to activate the photoactivatable substance. The light may be delivered in a manner to provide 360 degrees of light exposure to the object 620, for example to all sides and surfaces of the object 620. This may effectively kill pathogens on the object. The container 600 is then removed from the compartment and the solution 670 may be drained with the input device 640 by opening the valve 650. The object may be immediately removed from the bag 610 or may remain in the bag 610 for long term storage.

Figure 5:
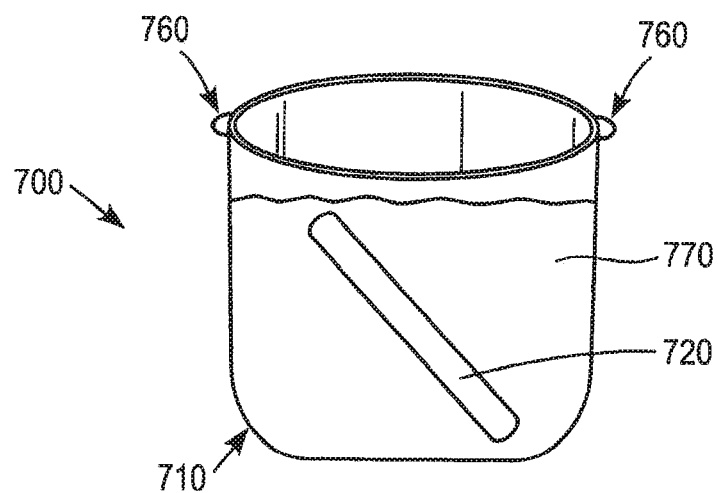
FIG. 5 shows an exemplary container in the form of a cup-like container.

FIG. 5 shows an exemplary container 700. The container 700 may be a cup-like container. The container 700 may include a cup 710. The cup 710 may be plastic. The cup 710 is adapted to hold a solution 770 and an object 720 to be treated. The cup 710 may be disposable. The cup 710 may include a holding device 760, such as a lip or ring around part or all the cup, hooks or loops. The cup 710 may have a lid (not shown) to allow sealing.

In an exemplary method, an object 720 is added to a container 700, in a cup 710. A solution 770 may be added to the cup 710. The solution is allowed to contact the object 720 for a sufficient period of time. The container 700 is applied to a compartment, such as compartment 70 in FIG. 1*a*. Light is applied to the compartment to activate the photoactivatable substance. The light may be delivered in a manner to provide 360 degrees of light exposure to the object 720, for example to all sides and surfaces of the object 720. This may effectively kill pathogens on the object. The container 700 is then removed from the compartment and the solution 770 may be drained from the cup. The object may be immediately removed from the cup 710 or may remain in the cup 710 for long term storage, the cup 710 being covered by a lid.

Figure 6:
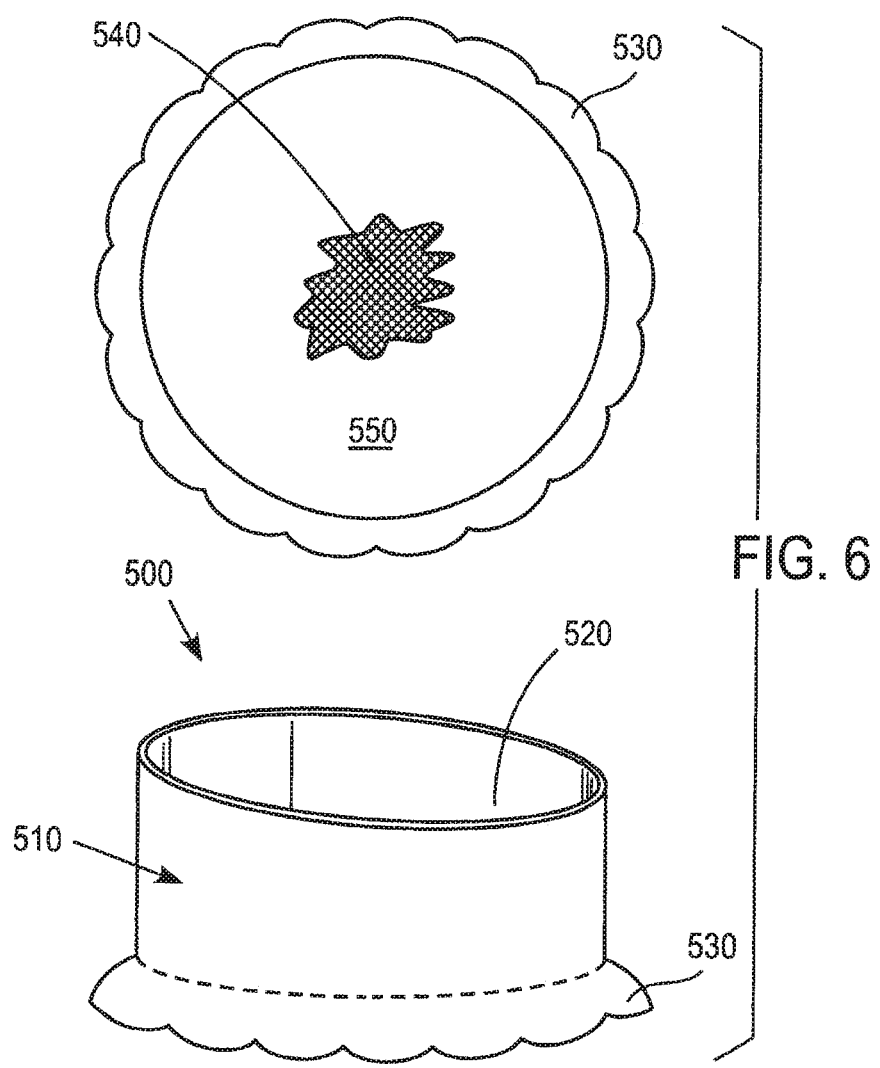
FIG. 6 shows an exemplary skin perfusion chamber.

FIG. 6 shows an exemplary device 500. The device 500 may be a skin perfusion chamber. The device has a side wall 510 that may be cylindrical shaped or otherwise shaped so as to form a chamber 520. The chamber 520 may not have a top so as to be an open chamber. The side wall 510 may include flaps 530 at the bottom portion. The flaps 530 may encircle the entire sidewall 510. The flaps 530 may be adhesive. The device 500 may be applied onto a skin surface 550, with the flaps 530 contacting the skin surface 550. A wound 540, such as an ulcer or lesion, may be on the skin surface in an area surrounded by the device 500.

In an exemplary method, a solution with a photoactivatable substance may be applied, such as by squirting or spraying, into the chamber 520 and onto the skin surface 550 and the wound 540. The adhesive flaps 530 and the side wall 510 maintain the solution in the chamber 520 to allow the solution to contact the wound 540 for a sufficient period of time. In an option, the device 500 is removed, allowing excess solution to drain off. A device, such as the device 300 from FIG. 2, is used to provide light onto the wound 540 to activate the photoactivatable substance. This may effectively kill pathogens on the wound.

Figure 7:
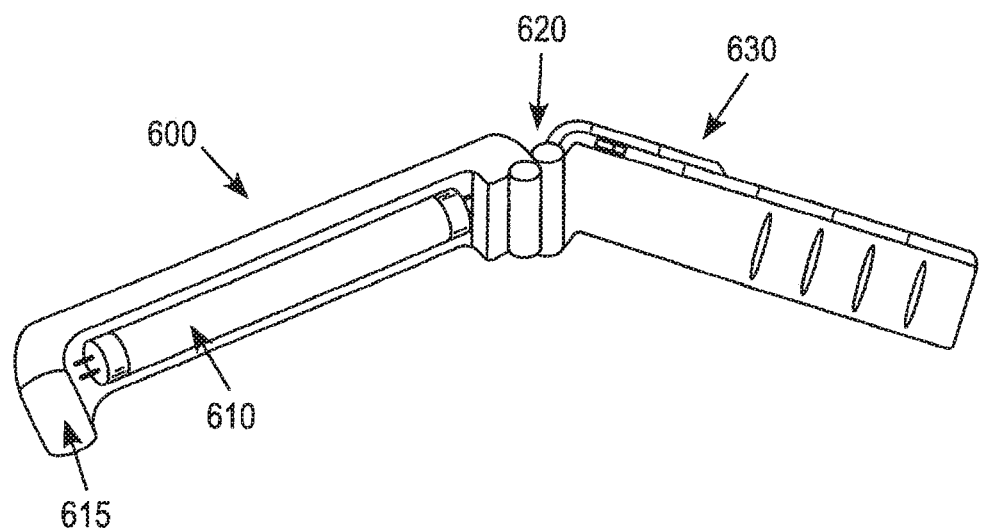
FIG. 7 shows an exemplary light for a flat surface.

FIG. 7 shows an exemplary device 600. The device 600 is adapted to introduce light onto a surface, for example a flat surface. A solution with a photoactivatable substance may be applied, such as by squirting or spraying, onto a surface, such as a countertop.

The device 600 includes a piece 630 which acts as a handle and may contain a power source, such as a battery. A hinge 620 (or a flexible arm) connects from the piece 630 to a light source 610. A cover 615 may cover the light source 610 on the sides, parts thereof, and the back.

In an exemplary method, a solution with a photoactivatable substance may be applied, such as by squirting or spraying, onto a surface, such as a countertop. The solution is allowed to contact the surface for a sufficient period of time. Then, the light source 610 is held and/or moved over the surface and powered to provide light onto the surface to activate the photoactivatable substance. This may effectively kill pathogens on the surface.

EXAMPLES

The contaminated instrument is placed in a chamber in the device. The chamber either contains or has introduced into it a fluid containing a photoactivatable substance. The photoactivatable substance will bind to the nucleic acid, i.e., the DNA or RNA of any pathogen which is present. The solution is composed of a 1% solution of riboflavin (vitamin B2).

A 5-20 minute incubation period occurs to permit binding of the photoactivatable substance to any pathogens. Then, photoactivation occurs through exposure to the UV (or visible) light source. The optimum wave length for the UV light is in the range of 373 nm and the intensity may be between 1 and 30 $J/cm^2$.

The light source is positioned so that the entire external surface of the instrument or object will be exposed to light i.e.: 360 degrees exposure. This is accomplished through the use of a specialized system of lights which include appropriate reflective surfaces. Following the previous step, which takes place over an approximately 5-20 minute period, the light source is turned off. Then, the fluid is drained from the container through an appropriate sterile valve system and the container labeled with the date of treatment and a designated number. The treated instrument will then be stored in the container to be opened upon use.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A device for decontaminating a medical device, the device comprising:
    a compartment containing a container holding a solution, the solution comprising a photoactivatable substance; and
    a light system which provides 360 degrees of light exposure to the container,
    wherein the light system provides light of about 320 nm to about 447 nm,
    wherein the device is configured for decontaminating the medical device while the entire medical device is in the solution by activating the photoactivatable substance in the solution with the light system.

2. The device of claim 1, wherein the compartment includes multiple light sources.

3. The device of claim 1, wherein essentially the entire interior surface of the compartment is reflective.

4. The device of claim 1, wherein the container is a bag system and wherein the device is configured to provide light exposure to all sides and surfaces of the bag system.

5. The device of claim 4, wherein the bag system includes a bag comprising a seal and an input device for inputting and/or drainage of the solution.

6. The device of claim 5, wherein the seal is resealable.

7. The device of claim 5, wherein the input device includes a valve to control when the input device is open or closed.

8. The device of claim 1, wherein the container is a cup system, and wherein the cup system is light permeable.

9. The device of claim 1, wherein the photoactivatable substance is riboflavin and the light system provides light of 373 nm.

10. A system for decontaminating a medical device, the system comprising:
 a solution, wherein the solution comprises a photoactivatable substance;
 a container, said container containing the solution, the container configured to contain the entire medical device in the solution; and
 a device, the device comprising:
  a compartment comprising the container and
  a light system which provides 360 degrees of exposure to the container,
 wherein the light system provides light of about 320 nm to about 447 nm,
 wherein the device is configured for decontaminating the medical device while the entire medical device is in the solution by activating the photoactivatable substance in the solution with the light system.

11. The system of claim 10, wherein the compartment includes multiple light sources.

12. The system of claim 10, wherein essentially the entire interior surface of the compartment is reflective.

13. The system of claim 10, wherein the photoactivatable substance is riboflavin and the light system provides light of 373 nm.

14. The system of claim 10, wherein the container is a bag system, wherein the device is configured to provide light exposure to all sides and surfaces of the bag system.

15. The system of claim 14, wherein the compartment comprises a holding system for holding the bag system in the compartment, wherein the holding system comprises hooks or loops.

* * * * *